US005792773A

United States Patent [19]
Chu et al.

[11] Patent Number: 5,792,773
[45] Date of Patent: Aug. 11, 1998

[54] L-β-DIOXOLANE URIDINE ANALOG ADMINISTRATION FOR TREATING EPSTEIN-BARR VIRUS INFECTION

[75] Inventors: Chung K. Chu, Athens, Ga.; Yung-Chi Cheng, Woodbridge, Conn.; Fucheng Qu, Lawrenceville, N.J.

[73] Assignees: Yale University, New Haven, Conn.; University of Georgia Research Foundation, Athens, Ga.

[21] Appl. No.: 749,263

[22] Filed: Nov. 15, 1996

[51] Int. Cl.$^6$ .................. A61K 31/505; A61K 31/70; C07D 473/00; C07H 19/10

[52] U.S. Cl. .................. 514/274; 514/50; 514/51; 536/26.23; 536/26.26; 536/26.8; 536/28.53; 536/28.54; 536/25.88; 544/242; 544/243

[58] Field of Search ................ 514/50, 51, 274; 536/26.8, 78.53, 78.54, 78.55, 26.23, 26.26; 544/242, 243

[56] References Cited

U.S. PATENT DOCUMENTS

| | | | |
|---|---|---|---|
| 5,041,449 | 8/1991 | Belleau et al. | 514/274 |
| 5,047,407 | 9/1991 | Belleau et al. | 514/274 |
| 5,151,426 | 9/1992 | Belleau et al. | 514/262 |
| 5,179,104 | 1/1993 | Chu et al. | 544/310 |
| 5,210,085 | 5/1993 | Liotta et al. | 514/274 |
| 5,248,776 | 9/1993 | Chu et al. | 544/310 |
| 5,270,315 | 12/1993 | Belleau et al. | 514/262 |

FOREIGN PATENT DOCUMENTS

| | | |
|---|---|---|
| 0337713 | 10/1989 | European Pat. Off. |
| 9214729 | 9/1992 | WIPO |
| 9404154 | 3/1994 | WIPO |

OTHER PUBLICATIONS

Lee et al., "Dioxolane Cytosine Nucleosides as Anti-Hepatitis B Agents," *Bioorganic & Medicinal Chem. Letters*, 5(17), 2011–2014 (Sep. 7, 1995).

Wilson et al., "The Synthesis and Anti-HIV Activity of Pyrimidine Dioxolanyl Nucleosides," *Bioorganic & Medicinal Chem. Letters*, 3(2), 169–174 (Feb. 1993).

Kim et al., "Asymmetric Synthesis of 1, 3-Dioxolane-Pyrimidine Nucleosides and Their Anti-HIV Activity." *J. Medicinal Chem.*, 35(11), 1987–1995 (May 29, 1992).

Kim et al., (II), L-β-(2S,4S)-and L-α-(2S,4R)-Dioxolanyl Nucleosides as Potential Anti-HIV Agents: Asymmetric Synthesis and Structure-Activity Relationships. *J. Medicinal Chem.*, 36(5), 519–528 (Mar. 5, 1993).

Chu et al. (III), "Asymmetric Synthesis of Enantiomerically Pure (-)-(1'R,4'R)-Dioxolane-Thymine and Its Anti-HIV Activity." *Tetrahedron Letters*, 32(31), 3791–3794 (Jul. 29, 1991).

Choi et al., "In Situ Complexation Directs the Stereochemistry of N-Glycosylation in the Synthesis of Oxathiolanyl and Dioxolanyl Nucleosides Analogues." *J. American Chem. Soc.*, 113(24), 9377–9379 (Nov. 20, 1991).

S. Balakrishna Pai, et al., "Inhibition of Hepatitis B Virus by a Novel L-Nucleoside, 2'-Fluoro-5-Methyl-β-L-Arabinofuranosyl Yracil," *Antimicrobial Agnets and Chemotherapy*, vol. 40, No. 2, Feb. 1996, pp. 380–386.

Gang-Qing Yao, et al., "Inhibition of Epstein-Barr Virus Replication by Novel L-Nucleoside, 2'-Fluoro-5-methyl-β-L-arabinofluranosyluracil." *Biochemical Pharmacology*, vol. 51, pp. 941–947. 1996. Month of publication data is unavailable.

*Primary Examiner*—John Kight
*Assistant Examiner*—L. Eric Crane
*Attorney, Agent, or Firm*—Henry D. Coleman; R. Neil Siebel

[57] ABSTRACT

The present invention relates to the discovery that certain β-L-dioxolane nucleoside analogs which contain a uracil base, and preferably, a 5-halosubstituted uracil base, exhibit unexpectedly high activity against Epstein-Barr virus (EBV). In particular, the compounds according to the present invention show potent inhibition of the replication of the virus (viral growth) in combination with very low toxicity to the host cells (i.e., animal or human tissue). Compounds are useful for treating EBV infections in humans.

7 Claims, 5 Drawing Sheets

FIGURE 1
Synthesis of L-Dioxolane Nucleosides
Scheme 1

FIGURE 2
Scheme 2

FIGURE 3
Scheme 3

L-β-DIOXOLANE URIDINE ANALOG ADMINISTRATION FOR TREATING EPSTEIN-BARR VIRUS INFECTION

FIELD OF THE INVENTION

This invention relates to novel L-β-Dioxolane Uridine nucleoside analogs and their use in the prevention and treatment of Epstein-Barr virus.

BACKGROUND OF THE INVENTION

As human bacterial infections have become more manageable and treatable through the use of increasingly available antibiotic agents, viral infections have remained a more difficult and less treatable target. Emphasis in finding agents to treat viral infections has remained a high priority.

Epstein-Barr virus (EBV is an important human pathogen, related to herpes simplex virus (HSV). Elliot Kieff, *Virology*, Third Edition, Edited by B. N. Fields, D. M. Knipe, P. M. Howley, et al. Epstein-Barr Virus and Its Replication. Chapter 74. Pp 2343–2396 and Alan B. Rickinson and Elliot Kieff, *Ibid.* Chapter 75, pp. 2397–2446. EBV is a lymphotrophic member of the genus Lumphocryptovirus, and belongs to the sub-family gammaherpesvirinae. Another new member of human virus also belonging to this family is Kaposi's sarcoma-associated herpes virus (KSHV/HHV8). Chang, et al., *Science*, 266:1865–1869 (1994); Cesarman, et al., *N. Eng. J. Med.*, 332:1186–1191 (1995); Soulier, et al., *Blood*, 86:1276–1280 (1995). There are two sub-types of EBV identified and their genomes are nearly identical, but there is no clear relationship between EBV associated diseases and EBV sub-types. Abdul-Hamid, et al., *Virology*, 190: 168–175 (1992) and Sample, et al., *J. Virol.*, 64:4084–4092 (1990). The lytic EBV genome is a linear, double-stranded, 172 Kbp DNA composed of 60 mol % guanine and cytosine. The genome has been sequenced and it was found to be capable of encoding a number of virus specified proteins, which include several enzymes involved in virus DNA synthesis during lytic infection of EBV. In vitro, EBV infection is generally limited to B-lymphocytes, although epithelial cells can also be infected. Sixbey, et al., *Nature*, 306:480–483 (1983). In humans, the virus genome can be detected in B-lymphocytes and T-lymphocytes as well as epithelial cells. The EBV genome replicates lytically in the linear form and can also be latent as supercoiled circular DNA. The expression of the EBV genome in lytic infected cells is very different from latent infected cells. EBV specified DNA plymerase, Dnase and dThd kinase are only expressed in cells upon lytic DNA replication. Cell culture studies indicated the essential role of EBV specified DNA polymerase for EBV DNA replication during lytic infection, but not for the maintenance of supercoiled EBV DNA in latent infected cells. A unique set of EBV proteins including EBVNA 1 and sometimes, EBNA LP, 2, 3A, 3B, 3C, LMP 1 as well as LMP2 is expressed in latent infected or transformed cells. Elliot Kieff, *Virology*, Third Edition, Edited by B. N. Fields, D. M. Knipe, P. M. Howley, et al. Epstein-Barr Virus and Its Replication. Chapter 74. Pp 2343–2396 and Alan B. Rickinson and Elliot Kieff, *Ibid.* Chapter 75, pp. H2397–2446.

Structurally, EBV is similar to that of other herpes viruses- it has a double-stranded DNA genome contained within a nucleocapsid, which is surrounded by a lipid envelope containing viral glycoproteins. A tegument protein occupies the space between the envelope and the nucleocapsid.

While primary EBV infection in infancy appears to be almost asymptomatic, a proportion (in some studies up to 50%) of serologically confirmed primary infections in adolescence or early adult life are manifested as infectious mononucleosis (IM) also called the "Kissing Disease". Transmission of EBV is primarily through the saliva, although some infections are transmitted via blood transfusions. A high percentage (>85%) of patients in the acute phase of infectious mononucleosis secrete EBV. In the mid-1970's, EBV was identified to cause fatal IM/X-linked lymphoproliferative syndrome (XLP) in young male children who had X-linked immunodeficiency. Sullivan and Wood, (*Immunodeficiency Rev.*, 1:325–347 (1989). Fatal EBV infection is also found to be associated with nonfamilial monophagocytic syndrome (VAHS) for which there is no effective therapy. Alan B. Rickinson and Elliot Kieff, *Virology*, Third Edition, Edited by B. N. Fields, D. M. Knipe, P. M. Howley, et al. Epstein-Barr Virus and Its Replication, Chapter 75, pp. 2397–2446 and Craig, et al., *Am. J. Clin. Path.*, 97:189–194 (1992).

Epstein-Barr virus is also recognized as a causative agent of B-cell proliferative diseases, and is linked to a variety of disease states, including a rare progressive mononucleosis-like syndrome and oral hair leukoplakia in AIDS patients. EBV has also been associated with certain types of cancer such as Burkitt's lymphoma, nasopharyngeal carcinoma, Hodgkin's disease, EBV-associated T-cell lymphoma and nasal T-cell lymphoma. Certain patients, in particular, those with suppressed immune systems such as AIDS patients and organ transplant patients who are being treated with immunosuppressive agents, are particularly susceptible to EBV manifestations, especially the development of EBV-associated lymphomas.

Chu, et al., in PCT application PCT/US95/01253, describe a number of L-nucleoside analogs for use in the treatment of Hepatitis B virus and Epstein-Barr virus infections. One agent disclosed in the PCT application, 2'-fluoro-5-methyl-β-L-arabinofuranosyluridine (L-FMAU), showed good activity against EBV. Noteworthy is the fact that when a 5-methyl group of L-FMAU was substituted with a bromo group, the anti-EBV activity decreased.

Several compounds have been shown to have activity against EBV replication in culture at concentrations nontoxic to cell growth. These include acyclovir (ACV), gancyclovir (DHPG), pencyclovir, D-FMAU and its analogs, 5-bromovinyl dUrd, phosphonoformate and phosphorothioate oligonucleotides. See Lin, et al., *Antimicrob. Agents and Chemo.* (February) 32(2):265–267 (1988); Lin, et al., *Antimicrob. Agents and Chemo.*, 32 (7):1068–1072 (1988); Cheng, et al., *Proc. Natl., Acad. Sci. USA*, 80:2767–2770 (1983); Datta, et al., *Proc. Natl., Acad. Sci. USA*, 77:5163–5166 (1980); Datta, et al., *Virology*, 114:52–59 (1981); Lin, et al., *Antimicrob. Agents and Chemo.*, 31:1431–1433 (1987); Olka and Calendar, *Virology*, 104:219–223 (1980); Lin, et al., *J. Virol.*, 50:50–55 (1984); Yao, et al., *Antimicrob. Agents and Chemo.*, 37:1420–1425 (1993) and Yao, et al., *Biochem. Pharm.*, (51):941–947 (1966).

OBJECTS OF THE INVENTION

It is an object of the present invention to provide compounds, pharmaceutical compositions and methods of treating and/or preventing Epstein-Barr virus infections in patients.

BRIEF DESCRIPTION OF THE INVENTION

The present invention relates to the discovery that certain β-L-dioxolane nucleoside analogs which contain a uracil base, and preferably, a 5-halosubstituted uracil base, exhibit unexpectedly high activity against Epstein-Barr virus (EBV). In particular, the compounds according to the present invention show potent inhibition of the replication of the virus (viral growth) in combination with very low toxicity to the host cells (i.e., animal or human tissue).

Compounds according to the present invention exhibit primary utility as agents for inhibiting the growth or replication of EBV. Certain of these agents also may be useful for inhibiting the growth or replication of other viruses (for example, HSV) or for treating other viral infections and/or related disease states. Other agents may be used as biological probes for testing purposes or as intermediates in the synthesis of related nucleoside compounds having pharmacological activity.

Compounds of the present invention find particular use in combating viral infections which afflict animals, and in particular, humans suffering from Epstein Barr virus infections. Compounds according to the present invention offer great potential as therapeutic agents against a disease state (EBV infections) for which there presently are few real therapeutic options. The compounds according to the present invention may be used alone or in combination with agents or other therapeutic treatments.

The compounds according to the present invention are dioxalone nucleoside analogs which contain an L-configuration (in contrast to the natural D- configuration of most naturally occurring nucleosides) and a uracil base. Preferably, the uracil base is substituted at the 5 position with a fluoro, chloro, bromo, iodo, methyl or trifluoromethyl, with a substitution at the 5 position of the uracil base with iodo or bromo being particularly preferred.

The present invention also relates to methods for inhibiting the growth or replication of IEBVcomprising exposing the virus to an inhibitory effective amount or concentration of at least one of the disclosed L-nucleoside analogs. This method may be used in comparison tests such as assays for determining the activities of related anti-EBV compounds as well for determining the susceptibility of a patient's EBV infection to one of the compounds according to the present invention. The present compounds are preferably used to treat or prevent EBV infections in humans.

The therapeutic aspect according to the present invention relates to methods for treating or preventing EBV infections in patients, preferably, human patients, comprising administering anti-viral effective amounts of one or more of the compounds according to the present invention to inhibit the growth or replication of the virus in the animal or human patient being treated. In a preferred method aspect according to the present invention, the present compositions are used to prevent or delay the onset of EBV-related lymphoma or cancer in patients, including those patients who have had a blood transfusion and those patients who are immunodeficient or immunocompromised, for example, AIDS patients and transplant patients, among others.

Pharmaceutical compositions based upon these novel chemical compounds comprise one or more of the above-described compounds in a therapeutically effective amount for treating a viral, generally, an EBV infection, optionally in combination with a pharmaceutically acceptable additive, carrier or excipient.

Certain of the compounds, in pharmaceutical dosage form, also may be used as prophylactic agents for inhibiting the growth or replication of EBV. These may be particularly appropriate as anti-EBV agents. In certain pharmaceutical dosage forms, the pro-drug form, for example, an acylated nucleoside or a nucleoside containing a phosphate ester may be preferred.

While not being limited by way of theory, it is believed that the compounds according to the present invention may induce their inhibitory effect on the growth or replication of EBV by inhibiting EBV DNA polymerase or by the incorporation of nucleosides into the EBV DNA which causes chain termination. It is unexpected that the present compounds, and in particular, the 5-iodo-L-nucleoside analog of the present invention, exhibits an anti-viral spectrum which is unlike any other nucleoside published in the literature so far. A distinguishing mechanism may be posited for the unique anti-viral activity.

The compounds according to the present invention are produced by synthetic methods which are readily known to those of ordinary skill in the art and include various chemical synthetic methods.

DETAILED DESCRIPTION OF THE INVENTION

The following definitions will be used throughout the specification to describe the present invention.

The term "patient" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

The term "pharmaceutically acceptable derivative" is used throughout the specification to describe any pharmaceutically acceptable salt or prodrug form (such as an ester, phosphate ester or salt of an ester) of a nucleoside compound which, upon administration to a patient, provides directly or indirectly the nucleo side compound or an active metabolite of the nucleoside compound. In general, the free nucleoside form or acyl prodrug forms of the present compounds, because of the presence of a uracil base, does not readily form salts. However, the mono-, di- and tri-phosphate forms of the nucleoside compounds according to the present invention will form salts on the phosphate moiety. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art.

The term "acyl" is used throughout the specification to describe a group at the 5' position of the nucleoside analog (i.e., at the free hydroxyl position in the dioxolanyl moiety) which contains a $C_1$ to $C_{20}$ linear, branched or cyclic alkyl chain. The acyl group at the 5' position, in combination with the 5' hydroxyl group results in an ester, which, after administration, may be cleaved to produce the free nucleoside form of the present invention. Acyl groups according to the present invention are represented by the structure:

$$R^2C(=O)-$$

where $R^2$ is a $C_1$ to $C_{20}$ linear, branched or cyclic alkyl chain, alkoxyalkyl, aryloxyalkyl, such as phenoxymethyl, aryl, alkoxy, among others. Preferred acyl groups are those where $R^2$ is $C_1$ to $C_3$. Acyl groups according to the present invention also include, for example, benzoyl, substituted benzoyl, such as 3-chlorobenzoyl, succinate, mesylate, caproyl, caproic, capric, lauric, myristic, palmitic, stearic and oleic, among others. One of ordinary skill in the art will recognize the acyl groups which will have utility in the present invention, either to synthesize the target pharmaceutical compounds or as prodrug of the nucleosides according to the present invention.

The term "phosphate ester" is used throughout the specification to describe monophosphate groups at the 5' position of the dioxanyl moiety which are esterified such that the phosphate group is rendered neutral, i.e., has a neutral charge. Phosphate esters for use in the present invention include those represented by the structure:

$$\text{Nucleoside-P}(=O)(OR^3)(OR^3)$$

where $R^3$ is selected from a $C_1$ to $C_{20}$ linear, branched or cyclic alkyl group, alkoxyalkyl, aryloxyalkyl, such as phenoxymethyl, aryl and alkoxy, among others. Preferred monophosphate esters for use in prodrug forms according to the present invention are those where $C_1$ to $C_{20}$ is a linear or branched chain alkyl group, most preferably a $C_1$ to $C_3$ alkyl group.

The term "inhibitory effective concentration" or "inhibitory effective amount" is used throughout the specification to describe concentrations or amounts of compounds according to the present invention which substantially or significantly inhibit the growth or replication of susceptible viruses, especially including EBV.

The term "therapeutic effective amount" or "therapeutically effective amount" is used throughout the specification to describe concentrations or amounts of compounds according to the present invention which are therapeutically effective in treating EBV infections in humans.

The term "preventing effective amount" is used throughout the specification to describe concentrations or amounts of compounds according to the present invention which are prophylactically effective in preventing or delaying the onset of EBV infections or related conditions (especially EBV-associated cancer or lymphoma) in humans.

The term "L-configuration" is used throughout the specification to describe the chemical configuration of the dioxolane uridine nucleoside compounds according to the present invention. The L-configuration of the sugar moiety of compounds of the present invention contrasts with the D-configuration of ribose sugar moieties of most naturally occurring nucleosides such as cytidine, adenosine, thymidine, guanosine and uridine.

The term "enantionmerically enriched" is used throughout the specification to describe a nucleoside which includes at least about 95%, preferably at least about 96%, more preferably at least about 97%, even more preferably, at least about 98%, and even more preferably at least about 99% or more of a single enantiomer of that nucleoside. When an L-nucleoside is referred to in this specification, it is presumed that the nucleoside is an enantiomerically enriched nucleoside, unless otherwise stated.

The present invention relates to the surprising discovery that the β-L-Dioxanyl Uridine nucleoside analogs which contain a dioxanyl moiety moiety having an L-configuration (as opposed to the naturally occurring D- configuration) exhibit unexpectedly strong activity against Epstein-Barr virus (EBV). In particular, the compounds according to the present invention show potent inhibition of the replication of the virus in combination with very low toxicity to the host cells (i.e., animal or human tissue).

The present invention also relates to the unexpected discovery that the compounds (2S,4S)-1-[(Hydroxymethyl) -1,3-dioxanyl-4-yl]-5-bromouracil (β-L-Br-OddU) and (2S, 4S)-1-[(Hydroxymethyl)-1,3-dioxanyl-4-yl]-5-iodouracil (β-L-I-OddU) are extremely effective anti-EBV agents exhibiting relatively low toxicity, especially compared to related D-nucleoside analogs which have been shown to exhibit anti-EBV activity.

The present invention, therefore relates to a group of compounds according to the structure:

where R is H, F, Cl, Br, I, $CH_3$ or $CF_3$; and $R^1$ is H, a $C_1$ to $C_{20}$ acyl or ether group, a phosphate, diphosphate, triphosphate or phosphate diester group.

In this aspect of the present invention, R is preferably Br or I and $R^1$ is H. Most preferably, R is I.

The present invention also relates to a method for inhibiting the growth or replication of Epstein-Barr virus (EBV) comprising exposing the virus to an inhibitory effective concentration of a compound according to the structure:

where R is H, F, Cl, Br, I, $CH_3$ or $CF_3$; and $R^1$ is H, a $C_1$ to $C_{20}$ acyl or ether group, a phosphate, diphosphate, triphosphate or phosphate diester group.

In this method aspect of the present invention, R is preferably Br or I, most preferably I and $R^1$ is most preferably H.

The present invention is also directed to a method for treating a patient suffering from an infection caused by the Epstein-Barr virus comprising administering to said patient a therepeutically effective concentration or amount of a compound according to the structure:

$$\begin{array}{c}\text{(structure shown)}\end{array}$$

where R is H, F, Cl, Br, I, $CH_3$ or $CF_3$; and $R^1$ is H, a $C_1$ to $C_{20}$ acyl or ether group, a phosphate, diphosphate, triphosphate or phosphate diester group.

In this method aspect of the present invention, R is preferably Br or I, most preferably I and $R^1$ is most preferably H.

The compounds according to the present invention are primarily usefuil for their anti-EBV activity. The present compounds may also be usefuil for other anti-viral activity. In addition, these compositions may also find use as intermediates in the chemical synthesis of other nucleoside or nucleotide analogs which are, in turn, useful as therapeutic agents or for other purposes, including their use in biological tests or as biological probes. Preferably, these compounds find use as novel anti-EBV agents.

In general, the most preferred anti-viral compounds according to the present invention include those which are less cytotoxic to the host cells and more active to the targeted virus. Certain of the compounds, in pharmaceutical dosage form, may be used as prophylactic agents. These may be particularly appropriate as anti-EBV agents. Because of their very low toxicity to the patient and excellent anti-EBV activity, βB-L-Br-OddU and β-L-I-OddU are especially effective anti-prophylactic compounds for treating and /or preventing EBV infections.

The compounds according to the present invention are produced by synthetic methods which are readily known to those of ordinary skill in the art and include various chemical synthetic methods as elaborated in significantly more detail in the Examples which follow. In general, compounds according to the present invention are synthesized by condensing a previously synthesized nucleoside base onto the appropriate dioxolanyl synthon which will ultimately give rise to a nucleoside analog having the desired L-configuration. In certain instances, the synthetic pathway may deviate from the general synthetic pathway for a specific nucleoside analog.

During chemical synthesis of the various compositions according to the present invention, one of ordinary skill in the art will be able to practice the present invention without undue experimentation. In particular, one of ordinary skill in the art will recognize the various steps that should be performed to introduce a particular substituent at the desired position of the base or a substituent at the desired position on the sugar moiety. In addition, chemical steps which are taken to "protect" functional groups such as hydroxyl or amino groups, among others, as well as "de-protect" these same functional groups, will be recognized as appropriate within the circumstances of the syntheses. A large number of protecting groups may be used in the present invention. In the case of the introduction of any one or more acyl groups onto the 5' position (or the uracil base) of the nucleoside, standard techniques, well known by those of ordinary skill, may be used. Synthesis of the 5'-mono, di- or triphosphates, or diesters of phosphates (as neutral prodrug forms), may also be synthesized by well-known methods in the art.

Figure 1:
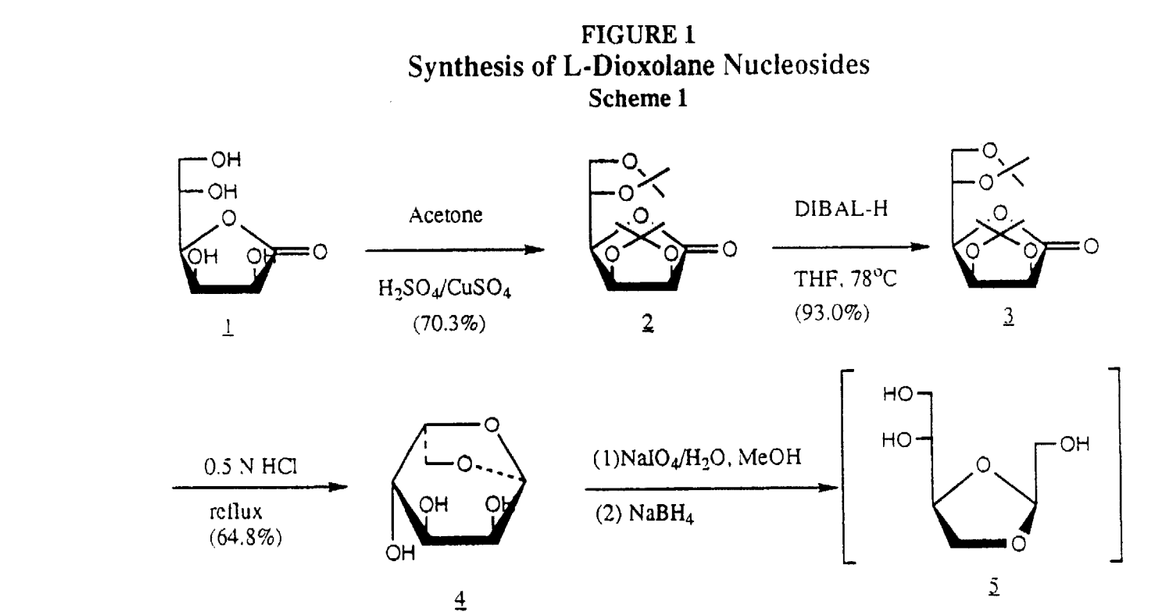
FIG. 1, scheme 1, depicts the chemical synthesis of dioxolanyl sugar intermediate 5 from L-gulono-γ-lactone 1.
Figure 2:
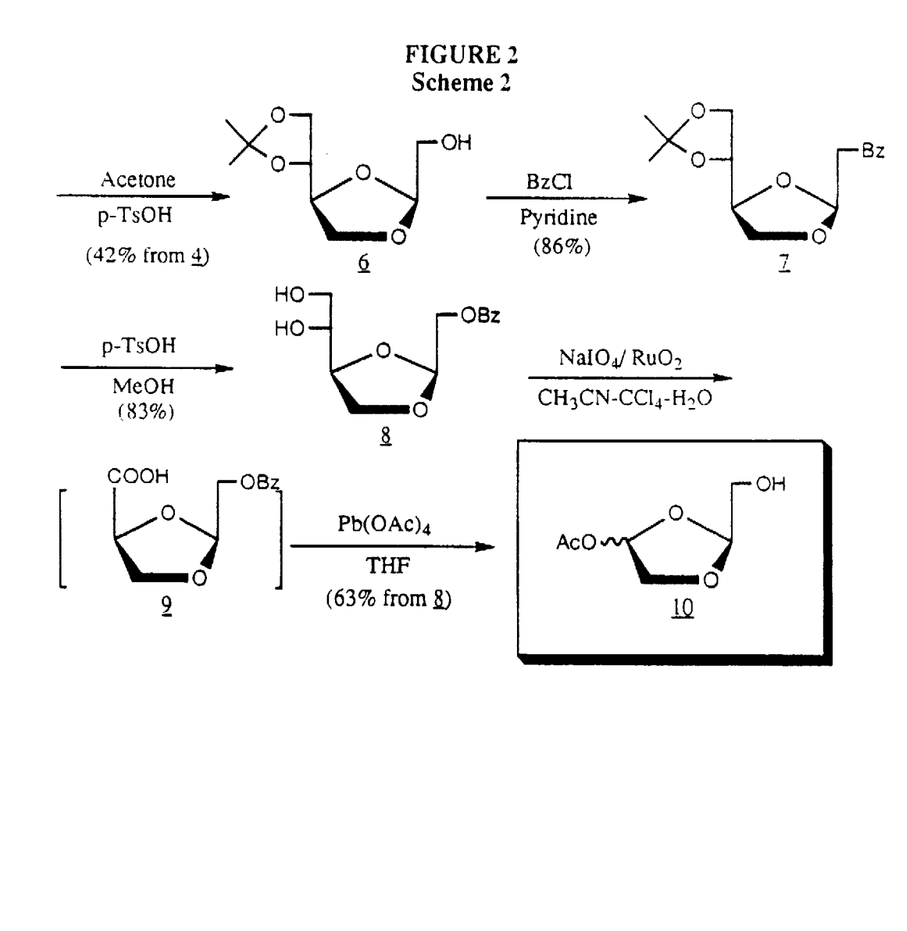
FIG. 2, scheme 2, depicts the chemical synthesis of an anomeric mixture of acetylated dioxolanyl sugar derivative 10 from 1,6-anhydro-β-L-gulopyranose 4.
Figure 3:
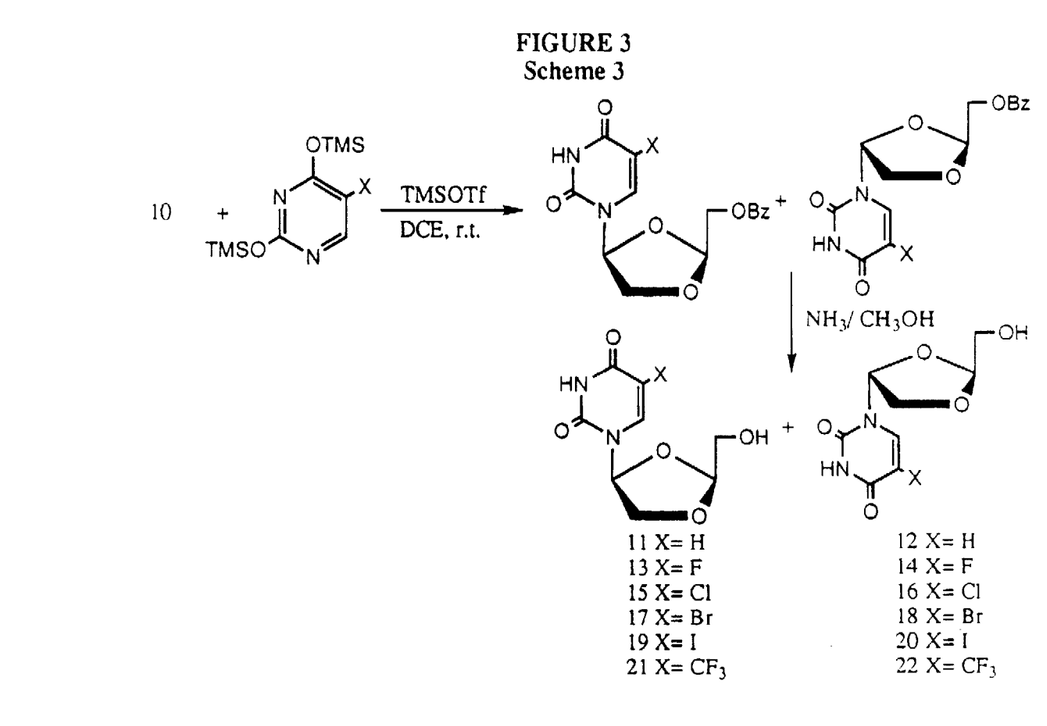
FIG. 3, scheme 3, depicts the chemical synthesis of the 5-substituted-β-L-dioxolanyl nucleoside analogs of the present invention (11, 13, 15, 17, 19 and 21) from dioxolanyl sugar derivative 10 and the protected 5-substituted uracil base.

In general, synthesis of the compounds according to the present invention proceeds by first synthesizing the appropriate dioxolanyl synthon and then condensing the substituted base onto the dioxolanyl synthon. An appropriate synthetic approach for synthesizing the present invention may be found in attached schemes 1–3 and as is generally described in the examples. Various equivalent synthetic approaches may also be used in the synthesizing the present compounds.

The therapeutic aspect according to the present invention relates to methods for treating EBV infections in patients comprising administering anti-viral effective amounts of the compounds according to the present invention to inhibit the growth or replication of the viruses in the patient being treated.

In a preferred method aspect according to the present invention, the present compositions are used to prevent or delay the onset of EBV-related lymphoma or cancer in patients, including those patients who have had a blood transfusion and those patients who are immunodeficient or immunocompromised, for example, AIDS patients and transplant patients, among others. The method comprises administering to such a patient a prophylactically effective amount (which generally is the same as a therapeutically effective amount) of one or more of the compositions according to the present invention to the patient to delay or prevent an EBV infection.

Pharmaceutical compositions based upon these novel chemical compounds comprise the above-described compounds in a therapeutically effective amount for treating a viral, especially an EBV infection, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and ether derivatives, pyridine esters, phosphate esters and various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition, in its most preferred embodiment, an EBV infection. In general, a therapeutically effective amount of the present compound in pharmaceutical dosage form usually ranges from about 0.1 mg/kg to about 100 mg/kg or more, more preferably, slightly less than about 1 mg./kg. to about 25 mg./kg. of the patient or considerably more, depending upon the compound used, the condition or infection treated and the route of administration. In the case of EBV infections treated with β-L-Br-OddU or β-L-I-OddU, the compound is preferably administered in amounts ranging from about 1 mg/kg to about 25 mg/kg of the patient, depending upon the pharmacokinetics of the agent in the patient. This dosage range generally produces effective blood level concentrations of active compound which may range from about 0.05 to about 100 micrograms/cc of blood in the patient. For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prod-drug forms of the nucleoside compounds according to the present invention.

In particularly preferred embodiments according to the present invention, the compounds and compositions are used to treat, prevent or delay the onset of viral infections of mammals and in particular EBV infections in humans. In its most preferred embodiment, the compounds are used to treat EBV infections, including chronic EBV infection. Preferably, to treat, prevent or delay the onset of EBV infections, the compositions will be administered in oral dosage form in amounts ranging from about 250 micrograms up to about 500 mg or more at least once a day, preferably, up to four times a day. The present compounds are preferably administered orally, but may be administered parenterally, topically or in suppository form.

The compounds according to the present invention, because of their low toxicity to host cells, may advantageously be employed prophylactically to prevent EBV infection or to prevent the occurrence of clinical symptoms associated with the viral infection. Thus, the present invention also encompasses methods for the prophylactic treatment of viral infections, and in particular EBV infections. In this aspect according to the present invention, the present compositions are used to prevent or delay the onset of an EBV infection or an EBV-related diseases such as lymphoma or cancer in patients, including those patients who have had a blood transfusion and those patients who are immunodeficient or immunocompromised, for example, AIDS patients and transplant patients, among others. This prophylactic method comprises administering to a patient in need of such treatment or who is at risk for the development of EBV-related symptoms or diseases an amount of a compound according to the present invention effective for alleviating, preventing or delaying the onset of the the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of β-L-Br-OddU and β-L-I-OddU, more preferably, β-L-I-OddU, these compounds may be administered within the same dosage range for therapeutic treatment (i.e., about 250 micrograms up to about 500 mg. or more from one to four times per day for an oral dosage form) as a prophylactic agent to prevent the proliferation of EBV or alternatively, to prolong the onset of an EBV infection which manifests itself in clinical symptoms.

In addition, compounds according to the present invention may be administered alone or in combination with other agents, especially including other compounds of the present invention. Certain compounds according to the present invention may be effective for enhancing the biological activity of certain agents according to the present invention by reducing the metabolism or inactivation of other compounds and as such, are co-administered for this intended effect.

In a particularly preferred pharmaceutical composition and method for treating EBV infections, an inhibitory effective amount of β-L-Br-OddU or β-L-I-OddU is administered to a patient suffering from an EBV infection to alleviate the symptoms of such infection.

In a particularly preferred pharmaceutical composition and method for treating EBV infections, an inhibitory effective amount of β-L-I-OddU is administered to a patient suffering from an EBV infection to alleviate the symptoms of such infection.

While not being limited by way of theory, it is believed that the compounds according to the present invention primarily induce their inhibitory effect on the growth or replication of EBV by functioning to inhibit EBV DNA polymerase or by incorporation of the nucleoside compounds into the EBV DNA which causes chain termination.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Synthesis of L-Dioxolanyl Pyrimidine Nucleosides

In general, compounds of the present invention are synthesized according to the chemical synthetic method described hereinbelow. The synthetic chemical methodology employed to synthesize the present compounds represents modifications of literature procedures. The references from which a related chemical reaction have been modified to produce the present compounds are set forth in the examples, below.

Melting points were determined on a Mel-temp II laboratory device and are uncorrected. NMR spectra were recorded on a Bruker 250 or Brucker 400 Fourier transform spectrometer; chemical shifts are reported in parts per million($\delta$), and signals are quoted as s (singlet), d (doublet), t (triplet), q (quartet), m (multiplet), and dd (doublet of doublets). UV spectra were obtained on a Beckman DU-7 spectrophotometer. Optical rotations were measured on a JASCO DIP-370 digital polarimeter. TLC was performed on Uniplates(silica gel) purchased from Analtech Co. Elemental analyses were performed by Atlantic Microlab, Inc., Norcross, Ga. Dry 1,2-dichloroethane, dichloromethane, acetonitrile, benzene and pyridine were obtained by distillation from $CaH_2$ prior to use. Dry THF was obtained by distillation from Na and benzophenone when the solution became purple.

Synthesis of 2,3,5,6-diisopropylidene-L-gulono-γ-lactone (2)

To a 5 L three-necked flask equipped with a mechanical stirrer were added L-gulono-γ-lactone 1 (100 g, 0.56 mol), anhydrous cupric sulphate (279 g) and anhydrous acetone (2.5 L, dried over 4 Å molecular sieves) successively. After starting stirring conc. $H_2SO_4$(10 mL) was added. The reaction mixture was stirred for 24 h under $N_2$ atmosphere. The mixture was neutralized with solid $Na_2CO_3$ and filtered. The filtrate was concentrated to dryness and the residue partitioned between $CH_2Cl_2$ (300 mL×3) and $H_2O$ (300 mL). The combined organic layer was washed with $H_2O$ (300 mL) and sat. $Na_2CO_3$ (250 mL), dried over $Na_2SO_4$. Filtered, concentrated to a syrup, $CH_2Cl_2$ (200 mL) was added to dissolve the residue and then hexane was added until the solution became turbid. The solid was filtered and washed with hexane. Three portions were combined and dried in vacuo. A total of 101.84 g of the product 2 was obtained (70.3%, $R_f$=0.77, $CHCl_3$/MeOH, 10:1).

Synthesis of 2,3,5,6-Diisopropylidene-L-gulono-γ-lactol (3)

To a 3 L, three-necked flask which was dried in oven and then purged with nitrogen, anhydrous THF(1 L) and the protected lactone 2 (101.84 g, 0.39 mol) were added. The solution was stirred and cooled with a dry ice-acetone cooling bath. After the temperature of the solution dropped to −78° C., DIBAL-H (500 mL,1M in hexane) was added dropwise via a dropping funnel under $N_2$ atmosphere. The mixture was stirred for 2 h, then methanol(140 mL) was added to quench the reaction. A large white lump was formed. Saturated potassium sodium tartrate solution was added until the solid disappeared. The organic layer was separated, the water layer was extracted with EtOAc (300 mL×2). The combined organic layer was washed with $H_2O$ (400 mL), sat. $NaHCO3$ (250 mL) and brine(250 mL), dried over anhydrous $Na_2SO_4$. Filtered, evaporation of the solvent under reduced pressure afforded white solid which was purified over column (silica gel, $CH_3OH/CH_2Cl_2$, 5–10%) to give the product 3 (95.05 g, 93%, $R_f$=0.64, $CH_3OH$/$CHCl_3$,1:10)

1,6-anhydro-β-L-gulopyranose (4)

To a 2 L flask were added lactol 3 (95 g, 0.36 mol) and 0.5N HCl (950 mL, 0.47 mol). The solution was stirred under reflux for 24 h, then the mixture was cooled and neutralized to PH=6 by Dowex-2 resin ($HCO_3$-form) with air bubbling to remove $CO_2$ generated. The mixture was filtered and the resin was thoroughly rinsed with $H_2O$ (1000 mL). The combined filtrates were concentrated to dryness under reduced pressure and the resulting residue was co-evaporated with absolute alcohol until a foam solid was formed. The solid was purified over column(silica gel, $CH_3OH/CH_2Cl_2$ 10–25%) to afford a slightly yellow solid which was recrystallized from absolute alcohol to yield a colorless solid 4 (25.2 g, 42.2%, $R_f$=0.62 $CH_3OH/CHCl_3$ 1:3, m.p. 142–145OC). Another product, L-gulose (Rf=0.25 $CH_3OH/CHCl_3$) was washed down from the column with 50% $CH_3OH$—$CH_2Cl_2$ and concentrated to a black residue which was recycled under the same reaction conditions to afford 4 (13.5 g, 22.6%). The total yield is 64.8%. $^1HNMR$ (DMSO-d6): δ3.22–3.68 (m,4 H, H-2,-3,-4, and -6a), 3.83 (d, $J_{6b,6a}$=7.25 Hz,1 H,H-6b), 4.22(pseudo t, $J_{5,6a}$=4.61 and 4.18 Hz, 1 H, H-5), 4.46(d, $J_{2OH,2}$=6.59 Hz,1 H, 2-OH exchangeable with $D_2O$), 4.62 (d, $J_{3OH,3}$=5.28 Hz,1 H, 3-OH, exchangeable with $D_2O$), 5.07 (d, $J_{4-OH,4}$=4.84 Hz, 1 H, 4-OH,exchangeable with $D_2O$), 5.20 (d, $J_{1,2}$=2.19 Hz, 1 H, H-1).

(1 'S,2S,4S)-4-[(1,2-Dihydroxy-1,2-O-isopropylidene)ethyl]-2-(hydroxymethyl) dioxolane (6)

A solution of $NaIO4$ (5.5 g, 25.7 mmol, 1.4 equiv.) in H2O (70 mL) was added dropwise via a dropping funnel to a solution of 4 (3 g, 18.5 mmol) in MeOH (100 mL) for 10 min at 0° C. and the mnixture was stirred mechanically for 15 min. NaBH4 (2.1 g, 56 mmol) was added and the reaction mixture was stirred for an additional 10 min. The white solid was filtered off and the solid was washed with MeOH (100 mL). The combined filtrate was neutralized by 0.5N HCl at 0° C., then concentrated to dryness and the residue was co-evaporated with absolute alcohol (20 mL×5), further dried in vacuo overnight. MeOH(100 mL) was added to dissolve the residue, the white solid was filtered off, the filtrate was concentrated to dryness and then dry acetone (300 mL), p-TsOH.H$_2$O(4 g) were added. The reaction mixture was stirred for 2 h, then neutralized with Et$_3$N. Filtered, concentrated to a syrup, which was purified over column (silica gel, EtOAc-hexane, 1:1) to give 6 (1.6 g, 42%, R$_f$=0.71 EtOAc/Hx, 2:1) as a colorless oil.

$^1$HNMR(DMSO-d6): δ1.25 and 1.31 (2 s, 2×3 H, isopropylidene), 3–39 (dd,J$_{CH2OH,H2}$=3.86 Hz, J$_{CH2OH,OH}$= 6.09 Hz, 2 H, —CH$_2$OH), 3.61–4.10 (m, 6 H, H-4,-5,-1' and -2',), 4.82 (t, $_{JH2,CH2OH}$ =3.87 Hz, 1 H, H-2), 4.90 (t, J$_{OH,CH2OH}$ =6.09 Hz, 1 H, —OH, exchangeable with D$_2$O)

(1 'S,2S,4S)-4- |(1,2-Dihydroxy-1,2-O-isopropylidene)ethyl|-2|(benzoyloxy)methyl| dioxolane (7)

Benzoyl chloride (4.4 mL, 37.5 mmol) was added dropwise via a syringe toa solution of 6 (5.7 g, 28 mmol) in pyridine-CH$_2$Cl$_2$ (1:2, 80 mL) at 0° C. under N$_2$ atmosphere. The temperature was raised to room temperature. After stirring for 2 h, TLC indicated the reaction was complete and the reaction was quenched with MeOH(10 mL). The solution was concentrated to dryness, the resulting residue was dissolved in CH$_2$Cl$_2$ (300 mL) and washed with H$_2$O (100 mL×2), brine(100 mL), dried over Na2SO4, filtered, and evaporated to give a yellow syrup, which was purified by silica gel column chromatography (EtOAc/Hx, 5–20%) to yield 7 (7.39 g, 86%, R$_f$=0.48, EtOAc/Hx, 1:3) as a colorless oil. 1HNMR (CDCl$_3$): δ1.35 and 1.44 (2s, 2×3 H, isopropylidene), 3.77–4.51 (m, 8 H, H-4, H-5, H-1', CH$_2$OBz), 5.29 (t, J=3.78 Hz, 1 H, H-2), 7.40–7.60, 8.05–8.09 (m,3 H, 2 H, OBz).

(1 'S,2S,4S)-4-(1,2-Dihydroxyethyl)-2-[(benzoyloxy)methyl]dioxolane (8)

To a stirred solution of 7 (13.62 g, 45 mmol) in MeOH (30 mL) was added p-TsOH (1.3 g, 6 mmol). The reaction mixture was stirred at room temperature for 2 h, TLC showed the reaction was incomplete. Solvents were evaporated to half volume, MeOH (50 mL) and p-TsOH (0.65 g) were added. After stirring for an additional 1 h, the reaction mixture was neutralized with Et3N and evaporated to dryness. The residue was purified by silica gel column chromatography (EtOAc/Hx, 10–15%) to give 8 (9.8 g, 83%, R$_f$=0.31, EtOAc /Hx, 2:1) as a colorless oil.

$^1$HNMR)(DMSO-d6): 6 3.43 (m, 2 H, H-2'), 3.67–4.1 (m, 4 H, H-4,-5,-1'), 4.32 (d,J=3.73 Hz,2 H, CH2OBz), 4.60 (t, J=5.72 Hz, 2'-OH, exchangeable with D2O), 5.23 (t, J=3.96 H.z,1 H,H-2), 7.45–7.7, 7.93–8.04 (m,3 H, 2 H, OBz).

(2S,4S)- and (2S,4R)-4-Acetoxy-2-[(benzoyloxy) methyl]dioxolane (10)

A solution of NaIO$_4$ (10.2 g, 48 mmol) in H$_2$O (120 mL) was added dropwise via a dropping funnel to a stirred solution of 8 (3.1 g, 11.0 mmol) in CCl$_4$.CH$_3$CN (1:1, 160 mL). Then RuO$_2$H$_2$O (0.03 g) was added. The reaction mixture was stirred for 5 h, TLC showed the reaction was complete, the solid was filtered off over Celite pad. The filtrate was evaporated to ⅓ volume, then CH$_2$Cl$_2$ (150 mL) was added, the organic layer was separated, and the water layer was extracted with CH$_2$Cl$_2$ (50 mL×3). The combined organic layer was washed with brine(100 mL), dried over MgSO$_4$. Filtered over Celite pad, then evaporated to dryness. The syrup was co-evaporated with dry THF (20 mL×5), further dried in vacuo overnight to give crude 9 (2.9 g).

The crude 9 was dissolved in dry THF (60 mL), then Pb(OAc)$_4$ (5.48 g, 12.4 mmol) and pyridine (0.83 mL, 10.3 mmol) was added under N$_2$ atmosphere. After the mixture was stirred for 1 h, TLC showed the reaction was complete. The solid was filtered off over Celite pad and washed with EtOAc(100 mL). The combined organic layer was evaporated to dryness, then purified by silica gel column chromatography (EtOAc/Hx, 30–50%) to afford anomeric mixture of 10 (1.93 g, 63%, R$_f$=0.64 and 0.54, Hexane/EtOAc, 2:1) as a colorless oil. 1HNMR(CDCl$_3$): δ1.998, 2.11 (2s, 3H, Oac), 3.93, 4.33 (m, 2H,H-5), 4.43, 4.48 (2 d, J=3.73, 3.74 Hz, 2 H, CH2OBz), 5.46, 5.55 (2 t, J=4.18, 3.63 Hz, 1 H, H-2), 6.42 (m, 1 H, H-4), 7.33–7.59, 8.00–8.15 (m,3 H, 2 H, -OBz).

(2S,4S)-1-|2-(Hydroxymethyl)-1,3-dioxolan-4-yl| uracil (11) and (2S,4R)-1-|2-(Hydroxymethyl)-1,3-dioxola-4-yl|uracil (12)

A mixture of uracil (0.63 g, 5.6 mmol) and HMDS (25 mL), (NH$_4$)$_2$SO$_4$ (5 mg) was refluxed under N$_2$ atmosphere for 5 h. The resulting clear solution was concentrated in vacuo under anhydrous condition to get an oil (silylated uracil), which was dissolved in dry DCE(10 mL). Under N$_2$ atmosphere dioxolane acetate 10 (1 g, 3.7 mmol) was added, then TMSOTf(1.4 mL) was added. The mixture was stirred for 2 h at room temperature then quenched by adding saturated aq. NaHCO$_3$(10 mL). The reaction mixture was stirred for another 30 min. The mixture was diluted with H$_2$O (50 mL) and CH$_2$Cl$_2$ (100 mL). The organic phase was separated, the water layer was extracted with CH$_2$Cl$_2$ (80 mL×3). The combined organic layer was washed with saturated aq. NaHCO$_3$ (150 mL), H$_2$O (100 mL), dried (MgSO4). Filtered, evaporation of solvent afforded a white solid (0.936 g, yield: 81%). The mixture was then treated with methanolic ammonia at room temperature for 24 h, then evaporated to dryness. The residue was purified by silica gel column chromatography using CH$_3$OH/CHCl$_3$ as the eluent to afford the 13 isomer 11, the a isomer 12 and an unseparated mixture of both isomers.

β-isomer 11: R$_f$=0.31 (MeOH/CHCl3, 3:10). UV(H2O): (pH 7) 261.0 nm (ε10432), (pH 11) 260.5 nm (ε7931), (pH 2) 261.0 nm (ε10651) |(α]$_D$$^{25}$=E 20.93 (c 0.33, MeOH). $^1$HNMR (DMSO-d$_6$): δ11.32 (s, NH), 7.80 (d, J=8.2 Hz, 1 H, H-6), 6.19 (d, J=4.95 Hz, 1 H, H-4'), 5.61 (d, J=7.98 Hz, 1 H, H-5), 5.18 (t, 1 H, OH, exchangeable with D$_2$O), 4.90 (t, J=2.75 Hz, 1 H, H-2'), 4.02–4.05 (m, 2 H, H-5'), 3.62 (d, J=2.75 Hz, 2 H, H-6'). Anal. Calcd for C$_8$H$_{10}$O$_5$N$_2$: C, 44.86; H, 4.67; N,13.08. Found: C, 44.94; H, 4.78; N, 13.02. α isomer 12: R$_f$=0.35 (MeOH/CHCl$_3$, 3:10). UV(H$_2$O): (pH 7) 262.0 nm (ε10684), (pH 11) 261.5 nm (ε8246), (pH 2) 261.5 nm (ε11208) [α]$_D$$^{25}$ =–3.28 (c 0.72, MeOH). $^1$HNMR (DMSO-d6): δ11.37 (br.s, NH), 7.58 (d, J=7.92 Hz,1 H, H-6), 5.61 (d, J=8.17 Hz, 1 H, H-5), 6.13 (dd, J=5.43 Hz, J=2.98 Hz,1 H, H-4'), 5.43 (t, J=3.6 Hz, 1 H, H-2'), 5.01 (t, J=6.02 Hz, OH, exchangeable with D2O), 4.26 (dd, J=5.6 Hz, J=9.4 Hz, 1 H, H-5'), 4.05 (dd, J=2.9 Hz, J=9.3 Hz, 1 H, H-5'), 3.42 (m, 2 H, H-6'). Anal. Calcd for C$_8$H$_{10}$O$_5$N$_2$: C, 44.86; H, 4.67; N, 13.08. Found: C, 44.77; H, 4.65; N, 13.00.

The same procedure was applied to synthesize the other 5-substituted nucleosides by analogy.

The following sets forth the analytical data for the remaining L-nucleoside analogs:

(2S,4S)-1-|2-(Hydroxymethyl)-1,3-dioxolan-4-yl|-5 fluorouracil (13) and (2S,4R)-1-[2-(Hydroxymethyl) -1,3 dioxola-4-yl|-5-fluorouracil (14)

Data of β-isomer 13: R$_f$=0.54 (MeOH/CHCl3 1:4). UV(H2O): (pH 7) 268.0 nm (ε9966); (pH 11) 268.0 mn (ε7822); (pH 2) 268.0 nm (ε10128). $[\alpha]_D^{25}$=7.73 (c 0.25, MeOH). ¹HNMR(DMSO-d₆): δ11.85 (NH), 8.24 (d, 1 H, J=7.17 Hz, H-6), 6.17 (d, 1 H, J=5.58 Hz, H-4'), 5.33 (t, 1 H, 5'-OH exchangeable with D₂O), 4.90 (s, 1 H, H-2'), 4.28 (d, J=4.0 Hz, 1 H, H-5'), 4.04 (dd, J=4.0, 8.0 Hz, 1 H, H-5'), 3.68 (m, 2 H, H-6'). Anal. Calcd for $C_8H_9O_5N_2F$: C, 41.38; H, 3.88; N, 12.07. Found: C, 41.62; H, 4.01; N, 11.82.

Data of α-isomer 14: Rf=0.53 (MeOH/CHCl₃,1:4). UV(H2O): (pH 7) 268.5 nm (ε10214), (pH 11) 268.0 nm (ε8212), (pH 2) 268.5 nm (ε12223). $[\alpha]_D^{25}$=5.81 (c, 0.29, MeOH). ¹HNMR(DMSO-d₆): δ11.90 (NH), 7.88 (d, J=6.82 Hz, 1 H, H-6), 6.10 (m, 1 H, H-4'), 5.49 (t, 1 H, J=3.87 Hz, H-2'), 5.00 (t, 1 H, 5'-OH, D₂O exchangeable), 4.03–4.29 (m, 2 H, H-5'), 3.33 (m, 2 H, H-6').

Anal. Calcd for $C_8H_9O_5N_2F$: C, 41.38; H, 3.88; N, 12.07. Found: C, 41.45; H, 3.87; N, 12.04.

(2S,4S)-1-[2-(Hydroxymethyl)-1,3-dioxolan-4-yl]-5-chlorouracil (15) and (2S,4R)-1-[2-(Hydroxymethyl)-1,3-dioxola-4-yl]-5-chlorouracil (16)

Data of β-isomer 15: Rf=0.61 (MeOH/CHCl₃, 1:4). UV(H2O): (pH 7) 275.0 nm (ε9018), (pH 11) 274.5 nm (ε7408), (pH 2) 276.0 nm (ε10432). $[\alpha]_D^{25}$ =2.98 (c 0.26, MeOH). ¹HNMR(DMSO-d6): δ 11.86 (NH), 8.37 (s,1 H, H-6), 6.17 (d,J=5.23 Hz, H-4'), 5.37 (t, J=5.65 Hz, 1 H, 5'-OH, D2O exchangeable), 4.92 (s, 1 H, H2'), 4.02–4.34 (m, 2 H, H-5'), 3.66 (m, 2 H, H-6').

Anal. Calcd for $C_8H_9O_5N_2Cl$: C, 38.63; H, 3.62; N, 11.27. Found: C, 38.39; H, 3.78; N, 11.02.

Data of α-isomer 16: $R_f$=0.56 (MeOH/CHCl₃, 1:4). UV(H2O): (pH 7) 276.0 nm (ε9448), (pH 11) 274.5 nm (ε8276), (pH 2) 276.5 nm (ε9509). $[\alpha]_D^{25}$=5.28 (c 0.31, MeOH).1HNMR (DMSO-d6): δ11.67 (NH), 7.68 (s, 1 H, H-6), 5.90 (d, J=4.0 Hz, 1 H, H-4'), 5.31 (t, J=4.0 Hz, 1 H, H-2'), 4.76 (t, 1 H, 5'-OH, D₂O exchangeable), 4.10 (dd, J=4.0, 8.0 Hz, 1 H, H-5'), 3.92 (dd, J=4.0, 8.0 Hz, 1 H, H-5'), 3.24 (m, 2 H, H-6').

Anal. Calcd for $C_8H_9O_5N_2Cl$: C, 38.63; H, 3.62; N, 11.27. Found: C, 38.45; H, 3.75; N, 11.13.

(2S,4S)-1-[2-(Hydroxymethyl)-1,3-dioxolan-4-yl]-5-bromouracil (17) and (2S,4R)-1-[2-(Hydroxymethyl)-1,3-dioxola-4-yl]-5-bromouracil (18)

Data of, β-isomer 17: Rf=0.61 (MeOH/CHCl3, 1:4). UV(H2O): (pH 7) 277.0 nm (ε7229), (pH 11) 276.0 nm (ε6981), (pH 2) 278.5 nm (ε9939). $[\alpha]_D^{25}$=4.61 (c 0.28, MeOH). ¹HNMR(DMSO-d6): δ11.83 (NH), 8.45 (s,1 H, H-6), 6.16 (d, J=5.05 Hz, 1 H, H-4:'), 5.36 (t,1 H, 5'-OH, D₂O exchangeable), 4.92 (s, 1 H, H-2'), 4.01–4.34 (m, 2 H, H5'), 3.66 (m, 2 H, H-6').

Anal. Calcd for $C_8H_9O_5N_2Br$ 0.7 $CH_3OH$: C, 33.10; H, 3.74; N, 8.87. Found: C, 33.50; H, 3.34; N, 8.46.

Data of α-isomer 18: Rf=0.58 (MeOH/CHCl3, 1:4). UV(H₂O): (pH 7) 279.0 nm (ε11825), (pH 11) 276.0 nm (ε8438), (pH 2) 279.0 nm (ε11801). $[\alpha]D25$=3.67 (c 0.29, MeOH). ¹HNMR(DMSO-d6): δ11.88 (NH), 7.92 (s, 1 H, H-6), 6.07 (dd, 1 H, J=3.17 Hz, 5.4 z, H-4'), 5.50 (t, J=4.0 Hz, 1 H, H-2'), 5.01 (t, 1 H, 5'-OH, D₂O exchangeable), 4.27 (m, 2 H, H-5'), 3.41 (m, 2 H, H-6').

Anal. Calcd for $C_8H_9O_5N_2Br$: C, 32.77; H, 2.73; N, 9.56. Found: C, 32.71; H, 3.12; N, 9.45.

(2S,4S)-1-[2-(Hydroxymethyl)-1,3-dioxolan-4-yl]-5-iodouracil (19) and (2S,4R)-1-[2-(Hydroxymethyl)-1,3-dioxola-4-yl]-5-iodouracil 20)

Data of β-isomer 19: Rf=0.77 (MeOH/CHCl₃, 1:4). UV(H₂O): (pH 7) 285.0 nm (ε6628), (pH 11) 279.0 nm (ε5593), (pH 2) 287 nm (ε7350). $[\alpha]_D^{25}$=7.60 (c 0.25, MeOH).1HNMR(DMSO-d₆): δ11.64 (NH), 8.42 (s, 1 H, H-6), 6.16 (d, 1 H, J=4.0 Hz, H-4'), 5.30 (br. s, 1 H, 5'-OH, D₂O exchangeable), 4.93 (s, 1 H, H2'), 4.04–4.31 (m, 2 H, H-5'), 3.66 (m, 2 H, H-6').

Anal. Calcd for $C_8H_9O_5N_2$: C, 28.23; H, 2.65; N, 8.24. Found: C, 28.36; H, 2.66; N, 8.18.

Data of α-isomer 20: Rf=0.75 (MeOH/CHCl₃, 1:4). UV(H2O): (pH 7) 287.5 nm (ε8946), (pH 11) 278.5 nm (ε6383), (pH 2) 287.5 nm (ε9049). $[\epsilon]_D^{25}$=6.75 (c 0.33, MeOH). ¹HNMR(DMSO-d₆): δ11.64 (NH), 7.75 (s, 1 H, H-6), 5.92 (dd, 1 H, J=4.0 Hz, H-4'), 5.32 (t, J=4.0 Hz, 1 H, H-2'), 4.78 (t, 1 H, 5'-OH, D₂O exchangeable), 4.12 (dd, J=4.0, 8.0 Hz, 1 H, H-5'), 3.95 (dd, J=4.0, 8.0 Hz, 1 H, H-5'), 3.25 (m, 2 H, H-6').

Anal. Calcd for $C_8H_9O_5N_2I$: C, 28.23; H, 2.65; N, 8.24. Found: C, 28.23; H, 2.73; N, 8.17.

(2S,4S)-1-[2-(Hydroxymethyl)-1,3-dioxolan-4-yl]-5-trifluoromethyluracil (21) and (2S,4R)-1-[2-(Hydroxymethyl)-1,3-dioxola-4-yl]-5-trifluoromethyluracil (22)

Data of β-isomer 21: Rf=0.60 (MeOH/CHCl₃, 1:4). UV(H₂O): (pH 7) 261.0 nm (ε10657), (pH 11) 259.0 nm (ε7334), (pH 2) 261.0 nm (ε11036) [α|D25=−5.94 (c 0.27, MeOH). ¹HNMR (DMSO-d₆): δ 11.88 (NH), 8.84 (s, 1 H, H-6), 6.17 (d, J=4.9 Hz, 1 H, H-4'), 5.40 (t, J=5.47 Hz, 1 H, 5'-OH, D₂O exchangeable), 4.94 (s, 1 H, H-2'), 4.03–4.39 (m, 2 H, H-5'), 3.68 (m, 2 H, H-6').

Anal. Calcd for $C_9H_9O_5N_2F_3$.0.2 EtOH: C, 38.73; H, 3.50; N, 9.61. Found: C, 38.92; H, 3.36; N, 9.54.

Data of α-isomer 22: Rf=0.58 (MeOH/CHCl3, 1:4). UV(H₂O): (pH 7) 260.5 nm (ε12221), (pH 11) 259.5 nm (ε6750), (pH 2) 261.0 nm (ε12342). $[\alpha]_D^{25}$=−2.59 (c 0.26, MeOH). ¹HNMR(DMSO-d₆): δ11.76 (NH), 7.80 (s, 1 H, H-6), 5.91 (dd, 1 H, J=4.0 Hz, H-4'), 5.32 (t, J=4.0 Hz, 1 H, H-2'), 4.82 (t, 1 H, 5'-OH, D₂O exchangeable), 4.00–4.18 (m, 2 H, H-5'), 3.31 (m, 2 H, H-6').

Anal. Calcd for $C_9H_9O_5N_2F_3$.0.1H₂O:, 38.05; H, 3.24; N, 9.86. Found: C, 37.75; H, 3.31; N, 9.80.

Biological Activity of L-Nucleoside Analogs

L-OddT was found to be as active as L-FMAU against EBV. In our studies, when the 5-methyl group of L-FMAU was substituted by the Bromo group, the anti-EBV activity was actually decreased. This suggested that halogen substitution for a methyl group on the 5 position of the uracil base would actually decrease activity in the uridine L-nucleosides. In contrast, when the 5-methyl group of L-OddT was substituted by the Bromo group, the antiEBV activity was actually increased. This was an unexpected result. More detailed structure activity relationship and the biological activities of L-I-OddU and L-Br-OddU are set forth below.

PROCEDURE

Cell Cultures

A high yield of EBV producing cell line H1 derived from human P3HR1 cells was used in this study. Cells were cultured in RPMI medium supplemented with 10% dialyzed fetal bovine serum and 100 μg/ml Kanamycin and were grown at 37° C. in a humidified incubator containing 5% $CO_2$.

Exposure of H1 Cells to Drugs

H1 cells were maintained in logarithmic phase of growth for two days prior to the initiation of treatment. The H1 cells were seeded in 24 well plates at the density of $2 \times 10^5$ cells per well in 2 ml of fresh medium with or without drug treatment and were incubated at 37° C. for 5 days. Following the period of drug treatment the cells were pelleted and used to determine the inhibitory effect of drug on EBV DNA by slot blot assay.

Slot Blot Assay

A total of $4 \times 10^5$ H1 cells treated with the various nucleoside analogs (as set forth below) were lysed in 400 μl of 10 mM Tris-HCl (pH 7.5) solution by freezing, and thawing 3 times. The cell lysate was treated with RNAase A (at a final concentration of 50 μg/ml) at 37° C. for 30 minutes and then with proteinase K (at a final concentration of 100 μg/ml) at 55° C. for 2 hr. The samples were denatured by adjusting the final concentration to 0.4N NaOH/10 mM EDTA at pH 8.2. After heating for 10 minutes in a water bath at 100° C., the samples were spotted onto positively charged nylon membrane using a manifold. Then $\alpha$-$^{32}$p-dCTP labeled EBV ECORIC fragment was used as a probe for DNA hybridization. The same membranes were reprobed with human Alu DNA (BAMH1 fragment) after stripping the BBV ECORIC probe. Autoradiographic results were anlayzed by densitometry. The amount of EBV DNA in treated H1 cells was determined according to the ratio of EBV DNA to Alu DNA in comparison with non-treatment control H1 cells. The same membranes were used for assessment of toxicity to mitochondria by rehybridization with a mitochondrial DNA probe after removing the Alu DNA probe. See, for example. Yao, et al.. *Antimic. Agents and Chemo.*, July, 1993, p. 1420–1425; Yao, et al.. *Biochem. Pharm.*. Vol. 51, 941–947 (1996) (EBVassay); Doong, et al, *Proc. Natl. Acad. Sci. USA*, vol. 88, 8495–8499 (October, 1991); and Bridges, et al., *Biochem. Pharm.*, Vol. 51, 731–736 (cytotoxicity and mt DNA assays).

Pharmacokinetics L-Br-OddU in BDF1 Mice

Figure 5:
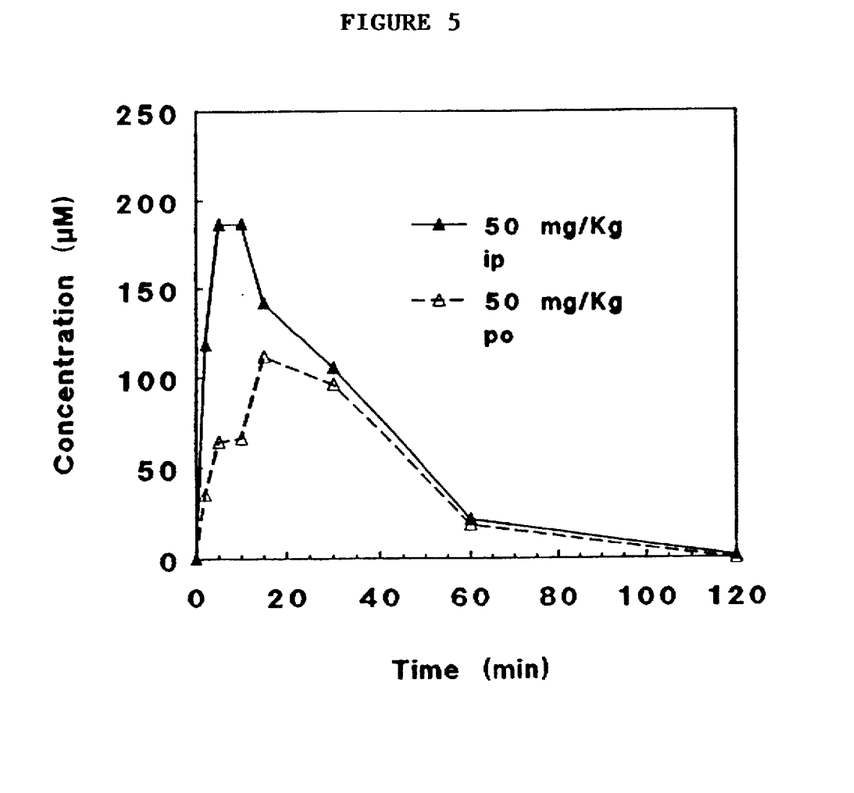
FIG. 5 is a graph depicting pharmacokinetic data generated for β-L-BrOddU in female BDF1 Mice.

Mice were treated with L-Br-OddU by administering 50 mg/kg orally (po), intraperitoneally (ip) and intravenously (iv). At the times indicated in FIG. 5, blood was drawn into a heparinized capillary from the retro orbital plexus of female BDF1 mice. The plasma was separated from the formed elements by centrifulgation. Then 100 l of plasma was mixed with an equal volume of 30% trichloracetic acid and kept on ice for 10 minutes. After centrifugation, the supernatant was moved to a clean tube and a 100 μl of a mixture of trioctylamine: freon (45%–55%) was mixed with the sample to extract the acid. The aqueous phase was moved to a clean tube and extracted again with the trioctylamine:freon mixture. Then 50 μl of the neutralized aqueous phase was injected onto a Perkin Elmer BPLC system. The samples were eluted from an Altech $C_{18}$ column with an isocratic solvent system of water at 2 ml per min. The concentrations of the unknown samples were determined by comparison with standards of known concentrations.

(1) Structure activity relationship of L-dioxolane uridine analogs against EBV, cell growth, and mitochondrial DNA (mt DNA) content.

Figure 4:
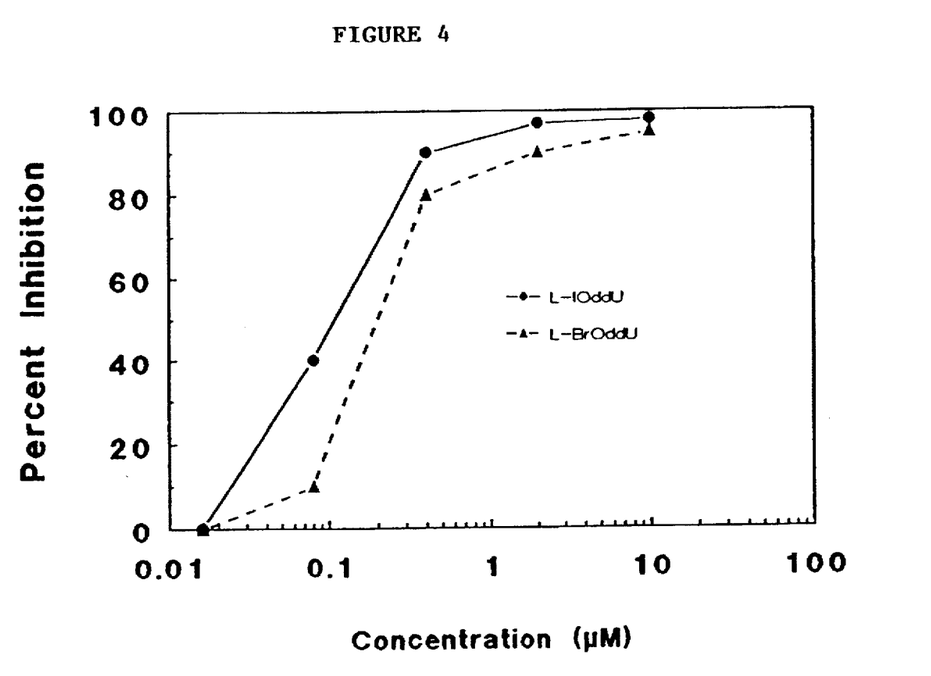
FIG. 4 is a graph depicting the dose response curves for the two most active compounds in the series against EBV, (2S,4S)-1-[(Hydroxymethyl)-1,3-dioxanyl-4-yl]-5-bromouracil (β-L-Br-OddU) and (2S,4S)-1-[(Hydroxymethyl)-1,3-dioxanyl-4-yl]-5-iodouracil (β-L-I-OddU).

Since L-OddT was found to be as active as L-FMAU against EBV, structural analogs containing halogen or hydrogen substitution for the 5 $CH_3$ as synthesized hereinabove were studied for their activities against EBVcell growth and toxicity to mt DNA (described above). The summary of the results is shown as follows and the dose response curve of the most active two compounds against EBV are shown in FIG. 4.

TABLE 2

| Abbreviation | R | Anti-EBV $EC_{50}$ μM | $EC_{50}$ μM | Cytotoxicity $IC_{50}$ μM | mt DNA Content $ID_{50}$ μM |
|---|---|---|---|---|---|
| L—OddU | H | >50 | — | >100 | Inactive |
| L—F—OddU | F | 50 | — | >100 | Inactive |
| L—Cl—OddU | Cl | 3 | — | >100 | Inactive |
| L—Br—OddU | Br | 0.2 | 2.0 | >100 | Inactive |
| L—I—OddU | I | 0.1 | 0.4 | >100 | Inactive |
| L—CF3—OddU | CF3 | 3 | — | >100 | Inactive |
| L—OddT | CH3 | ~5 | — | — | — |
| D—I—OddU | I | Inactive | — | — | — |
| D—Br—OddU | Br | Inactive | — | — | — |
| L—Br—OddC | | Inactive | — | — | — |
| ddC | | Inactive | | 20 | 0.02 |
| DHPG | | 5 | | 75 | Inactive |

Conclusion: L-Br-OddU and L-I-OddU are the most potent anti-EBV compounds examined. They have little effect on mitochondrial or nuclear DNA synthesis. This is reflected by their lack of effect on mitochondrial DNA content and cell growth as well as the lack of induction of lactate accumulation in the medium from the drug treated cultures. Their mirror image of compounds with the natural D-configuration were much less active against EBV. Furthermore, L-Br-OddC and L-I-OddC were also inactive against EBV.

(2) Spectrum of antiviral activity of L-I-OddU

The activity of L-I-OddU against other virus growth was examined. The summary results is shown as follows.

TABLE 3

| Virus | $EC_{50}$ μM |
|---|---|
| HSV-1 | $50_{\mu M}$ |
| HSV-2 | Inactive up to $50_{\mu M}$ |
| CMV | Inactive up to $10_{\mu M}$ |
| EBV | $0.1_{\mu M}$ |
| HBV | Inactive up to $10_{\mu M}$ |
| HIV | Inactive up to $100_{\mu M}$ |

Plaque reduction assays used for HSV-1, HSV-2 and CMV have been previously described. See, Gao, et al., *Antimic. Agents and Chemo.*, May, 1990, p. 808–812 (HSV-Plaque); Cheng, et al., *Proc. Natl. Acad. Sci. USA*, vol. 80, 2767–2770 (May 1983) (CMV plaque reduction assay). The methods for testing against EBV, HBV, and HIV were also used as described previously. See, Yao, et al.. *Antimic. Agents and Chemo.*, July, 1993, p. 1420–1425; Yao, et al., *Biochem. Pharm.*, Vol. 51, 941–947 (1996) (EBV assay); Doong, et al, *Proc. Natl. Acad. Sci. USA*, vol. 88, 8495–8499 (October, 1991) (BBV assay); Mellors, et al., *Molecular Pharm.*, 41:446–451 (1992) and Bridges, et al., *Biochem. Pharm.*, Vol. 51, 731–736 (HIV assay).

Unlike L-FMAU, which is active against EBV and BBV, L-I-OddU is only potently active against EBV with an $EC_{50}$ value at least for times lower than L-FMAU. Noteworthy is the fact that L-I-OddU showed little activity against HBV. The antiviral spectrum of L-I-OddU is different from any antiviral compound described so far in the literature. It also suggests that the action of this compound is specific for EBV.

(3) Dose Response of L-I-OddU and L-Br-OddU against EBV replication

H1 cells were exposed to these two compounds at the indicated dosage for five days. EBV DNA content of drug treated cells were estimated by slot blot hybridization technique as described above and compared with that of drug free cells. L-I-OddU is slightly more potent than L-Br-OddU against EBV DNA synthesis. Dose response curves for these analogs appear in FIG. 4.

(4) Stability of L-I-OddU at different pH's

In order to explore the possibility of using L-I-OddU orally for the treatment of EBV-associated diseases, its stability at different pH levels is important. L-I-OddU was exposed to different pH solutions as indicated for 3 hr at 37°. The percentage of compound remaining as L-I-OddU was examined using HPLC with a $C_{18}$ column.

TABLE 4

| | % Remaining | |
|---|---|---|
| | L—I—OddU | L—Br—OddU |
| pH1 | 102 | 105 |
| pH2 | 102 | — |
| pH5 | 102 | — |
| pH7 | 99 | — |
| pH9 | 100 | — |

This study strongly suggests that L-I-OddU may be useflul orally since it is stable at pH 2, thus able to pass into the upper small intestine (duodenum, jejunum, ileum) where it can be readily adsorbed without significant deactivation by stomach acid.

(5) Preliminary pharmacokinetic study of L-Br-OddU in mice

The pharmacokinetics of L-Br-OddU, which is as stable at pH1 as L-I-OddU, was examined in BDF1 mice. We did a preliminary pharmacokinetic study by giving 50 mg/kg orally (po), intraperitoneally (ip), and intravenously (iv) as described in greater detail, above. The multiphasic concentration curve of the ip and the iv groups were similar, therefore, only the ip curve is shown for simplicity. The plasma level is demonstrated in attached FIG. 5.

From this pharmacokinetic study, it can be concluded that L-Br-OddU could be taken up orally with an efficiency of about 60%, which is better than L-FMAU. It is anticipated that L-I-OddU will also have a similarly efficient oral uptake.

It is to be understood by those skilled in the art that the foregoing description and examples are illustrative of practicing the present invention, but are in no way limiting. Variations of the detail presented herein may be made without departing from the spirit and scope of the present invention as defined by the following claims.

We claim:

1. A method for treating Epstein-Barr virus infections in a patient comprising administering to said patient a therapeutically effective amount of a compound according to the structure:

where R is H, F, Cl, Br, I, $CH_3$ or $CF_3$; and $R^1$ is H, a $C_1$ to $C_{20}$ acyl or ether group, a phosphate, diphosphate, triphosphate or phosphodiester.

2. The method according to claim 1 where R is H, Br or I.

3. The method according to claim 1 where R is Br or I.

4. The method according to claim 1 where R is I.

5. The method according to claim 1 where $R^1$ is a $C_1$ to $C_3$ acyl group.

6. A method for treating an Epstein-Barr virus infection in a patient comprising administering to said patient a therapeutically effective amount of a compound according to the structure:

where R is Br or I and $R^1$ is H.

7. The method according to claim 6 where R is I.

* * * * *

UNITED STATES PATENT AND TRADEMARK OFFICE
CERTIFICATE OF CORRECTION

PATENT NO. : 5,792,773
DATED : August 11, 1998
INVENTOR(S) : Chu et al.

It is certified that error appears in the above-identified patent and that said Letters Patent is hereby corrected as shown below:

Column 1, line 8; after "Epstein-Barr virus.", insert the following lines: --Certain subject matter in this patent has been supported by NIH grant No. AI 33655. Consequently, the government retains certain rights in the invention.--

Signed and Sealed this

Second Day of February, 1999

Attest:

Attesting Officer

*Acting Commissioner of Patents and Trademarks*

UNITED STATES PATENT AND TRADEMARK OFFICE
CERTIFICATE OF CORRECTION

PATENT NO.    : 5,792,773
DATED         : August 11, 1998
INVENTOR(S)   : Chu et al.

It is certified that error appears in the above-identified patent and that said Letters Patent is hereby corrected as shown below:

Column 1,
Line 8, after "Epstein-Barr virus.", insert the following lines:
-- Certain subject matter in this patent has been supported by NIH grant No. AI 33655. Consequently, the government retains certain rights in the invention. --

Signed and Sealed this

Twenty-seventh Day of August, 2002

Attest:

Attesting Officer

JAMES E. ROGAN
Director of the United States Patent and Trademark Office